(12) United States Patent
Gant

(10) Patent No.: US 7,833,241 B2
(45) Date of Patent: Nov. 16, 2010

(54) SURGICAL SAW BLADE COUPLER

(75) Inventor: Andrew Gant, Austin, TX (US)

(73) Assignee: Stryker Corporation, Kalamazoo, MI (US)

( * ) Notice: Subject to any disclaimer, the term of this patent is extended or adjusted under 35 U.S.C. 154(b) by 509 days.

(21) Appl. No.: 10/700,256

(22) Filed: Nov. 3, 2003

(65) Prior Publication Data

US 2004/0204731 A1  Oct. 14, 2004

Related U.S. Application Data

(60) Provisional application No. 60/425,461, filed on Nov. 12, 2002.

(51) Int. Cl.
- A61B 17/14 (2006.01)
- B23D 49/00 (2006.01)
- B26B 1/00 (2006.01)

(52) U.S. Cl. .............................. 606/176; 30/392; 30/339

(58) Field of Classification Search ......... 606/176–180, 606/82, 167–172, 187; 30/331, 335–339, 30/180, 351, 355, 333, 166.3, 156, 388; 128/317; 279/76, 96, 101, 102, 44, 46.1, 279/19.6–19.7, 79, 80, 147, 16, 18, 97, 904; 403/92, 96, 97, 101
See application file for complete search history.

(56) References Cited

U.S. PATENT DOCUMENTS

| | | |
|---|---|---|
| 2,455,655 A | 12/1948 | Carroll |
| 2,795,247 A | 6/1957 | Topolinski |
| 3,905,105 A | 9/1975 | Tuke |
| 3,905,374 A | 9/1975 | Winter |
| 3,943,934 A | 3/1976 | Bent |
| 4,036,236 A | 7/1977 | Rhodes, Jr. |
| 4,069,824 A | 1/1978 | Weinstock |
| 4,106,181 A | 8/1978 | Mattchen |
| 4,386,609 A | 6/1983 | Mongeon |
| 4,513,742 A | 4/1985 | Arnegger |
| 4,584,999 A | 4/1986 | Arnegger |
| 4,617,930 A | 10/1986 | Saunders |
| 4,637,391 A | 1/1987 | Schlein |
| 4,703,751 A | 11/1987 | Pohl |
| 4,718,413 A | 1/1988 | Johnson |
| 4,750,481 A | 6/1988 | Reese |
| 4,768,504 A | 9/1988 | Ender |
| 5,122,142 A | 6/1992 | Pascaloff |
| 5,135,533 A | 8/1992 | Petersen et al. |
| 5,178,626 A | 1/1993 | Pappas |

(Continued)

Primary Examiner—Anhtuan T Nguyen
Assistant Examiner—Diane Yabut
(74) Attorney, Agent, or Firm—Howard & Howard Attorneys PLLC

(57) ABSTRACT

A surgical saw blade coupler for removably holding a surgical saw blade. The surgical saw blade may be of various shapes and sizes, including, but not limited to straight or crescentic. The surgical saw blade coupler includes a cap, a pin and a driver. The driver is rotatably coupled to a motor within a housing. A cup is located within the housing within a bearing. The cap and the pin form a slot which receives a first end of the surgical saw blade. The cap and the pin also form a groove for receiving a back edge of the surgical saw blade. The surgical saw blade coupler is moveable between an open position in which the surgical saw blade may be removed, exchanged or inserted, and a closed position. A biasing spring acts against a button and the pin to close the coupler.

20 Claims, 6 Drawing Sheets

U.S. PATENT DOCUMENTS

| | | | |
|---|---|---|---|
| 5,263,972 A * | 11/1993 | Evans et al. | 606/176 |
| D351,907 S | 10/1994 | Matthai et al. | |
| 5,366,312 A | 11/1994 | Raines | |
| 5,382,249 A * | 1/1995 | Fletcher | 606/79 |
| D360,946 S | 8/1995 | Goris | |
| D362,065 S | 9/1995 | Goris | |
| 5,468,247 A * | 11/1995 | Matthai et al. | 606/178 |
| 5,507,763 A | 4/1996 | Petersen et al. | |
| 5,554,165 A | 9/1996 | Raitt et al. | |
| 5,658,304 A * | 8/1997 | Lim | 606/176 |
| 5,694,693 A | 12/1997 | Hutchins et al. | |
| 5,729,904 A * | 3/1998 | Trott | 30/339 |
| 5,735,866 A | 4/1998 | Adams et al. | |
| 5,839,196 A * | 11/1998 | Trott | 30/339 |
| 6,022,353 A | 2/2000 | Fletcher et al. | |
| 6,051,009 A | 4/2000 | Hellenkamp et al. | |
| 2002/0198556 A1 | 12/2002 | Ark et al. | |

* cited by examiner

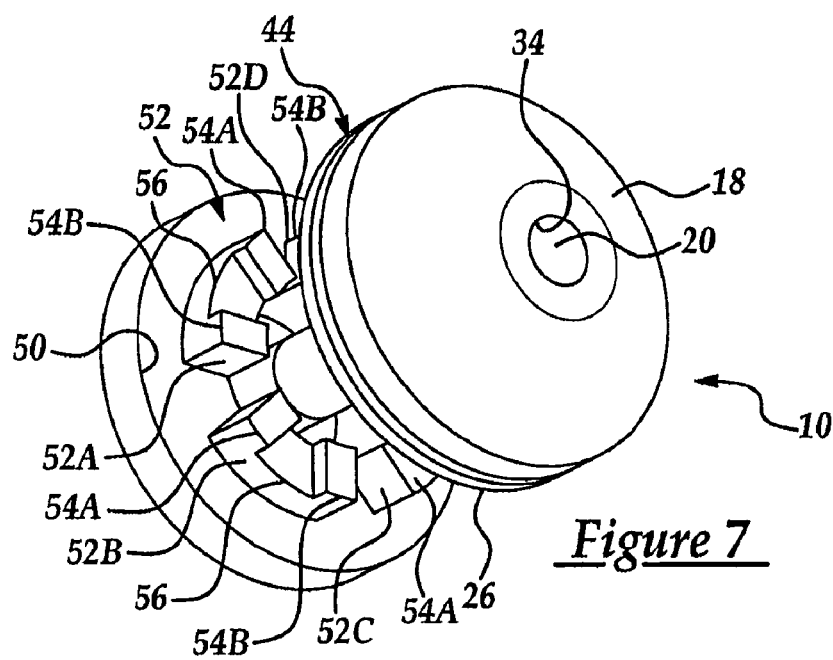
Figure 7
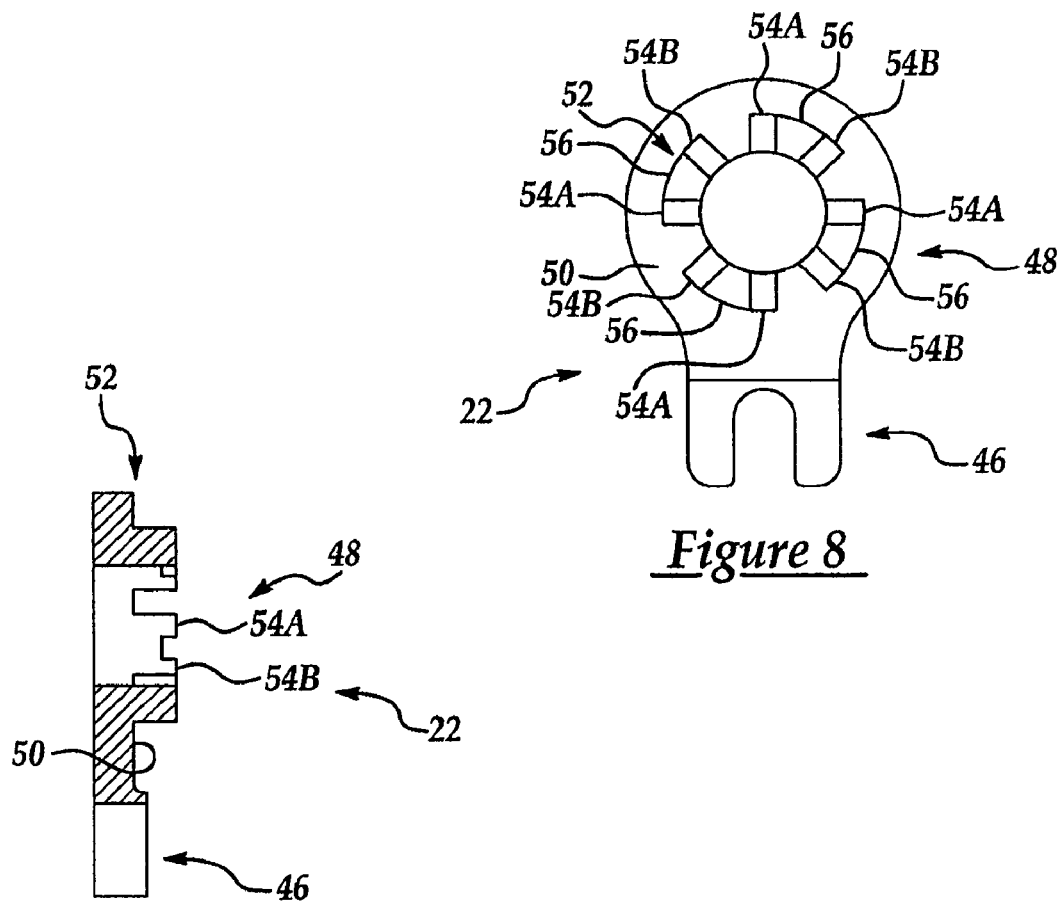
Figure 8
Figure 9

SURGICAL SAW BLADE COUPLER

CROSS-REFERENCE TO RELATED APPLICATIONS

The present application claims priority to U.S. Provisional Application Ser. No. 60/425,461, filed Nov. 12, 2002.

FIELD OF THE INVENTION

The present invention relates generally to powered surgical cutting devices, and more particularly, to a surgical saw blade coupler for releasably holding a surgical saw blade.

BACKGROUND OF THE INVENTION

It is common to use powered surgical cutting devices during surgical procedures. Generally, these devices have a handle. An electric or pneumatic motor is contained within the handle. The motor drives, in a cyclical fashion, a driver. One end of a surgical blade is releasably coupled to the driver. The other end of the blade includes a cutting edge with a plurality of teeth. The surgical blade may be of various shapes, e.g., for crescentic or straight and, typically, may be mounted to the driver in various positions. Commonly, the surgical blades are interchangeable and disposable.

Generally, a clamping structure is used to releasably couple the blade to the driver. When force is applied to the cutting edge of the surgical blade the force is transferred to the opposite end of the blade. This may have the effect of compromising the clamping structure, resulting in an unintentional release or slippage of the saw blade.

One device aimed at overcoming this problem is disclosed in U.S. Pat. No. 5,658,304 issued Aug. 19, 1997 to Joepert Lim (the '304 patent). The device disclosed in the Lim patent includes a cutting element with two flanges and a handpiece with a base surface and a groove adjacent the base surface. When coupled together, one of the flanges engages the base surface and the other flange engages the groove. However, the addition of a second flange to the saw blade, increases the complexity of the saw blade and thus the cost of the saw blade.

The present invention is aimed at one or more of the problems as set forth above.

SUMMARY OF THE INVENTION AND ADVANTAGES

A surgical saw blade coupler for removably holding a surgical saw blade. The surgical saw blade may be of various shapes and sizes, including, but not limited to straight or crescentic. The surgical saw blade coupler includes a cap, a pin and a driver. The driver is rotatably coupled to a motor within a housing. The cap and the pin form a slot which receives a first end of the surgical saw blade. The cap and the pin also form a groove for receiving a back edge of the surgical saw blade. The surgical saw blade coupler is moveable between an open position in which the surgical saw blade may be removed, exchanged or inserted, and a closed position.

BRIEF DESCRIPTION OF THE DRAWINGS

Other advantages of the present invention will be readily appreciated as the same becomes better understood by reference to the following detailed description when considered in connection with the accompanying drawings wherein:

FIG. 7 is an enlarged view of the surgical saw blade coupler of FIG. 1 in an open position;

FIG. 8 is a top view of a driver of the surgical saw blade coupler of FIG. 1, according to an embodiment of the present invention;

FIG. 9 is a side view of the driver of FIG. 8;

DETAILED DESCRIPTION OF THE INVENTION

With reference to the drawings, and in operation, the present invention provides a surgical saw blade coupler 10 for use with a surgical saw blade 12. As discussed below, the surgical saw blade 12 may be of various shapes and sizes, such as a crescentic blade or a straight blade. The surgical saw blade coupler 10 is partially, rotatably contained within a housing 14 and is coupled to a motor (not shown) contained within the housing 14. The motor may be of any suitable type, e.g., pneumatic or electrical. The motor provides motion to the surgical saw blade 12. In one embodiment, the motor provides cyclical linear motion. In another embodiment, the motor provides cyclical angular motion (as shown by the arrow 16 in FIG. 1).

Figure 3:
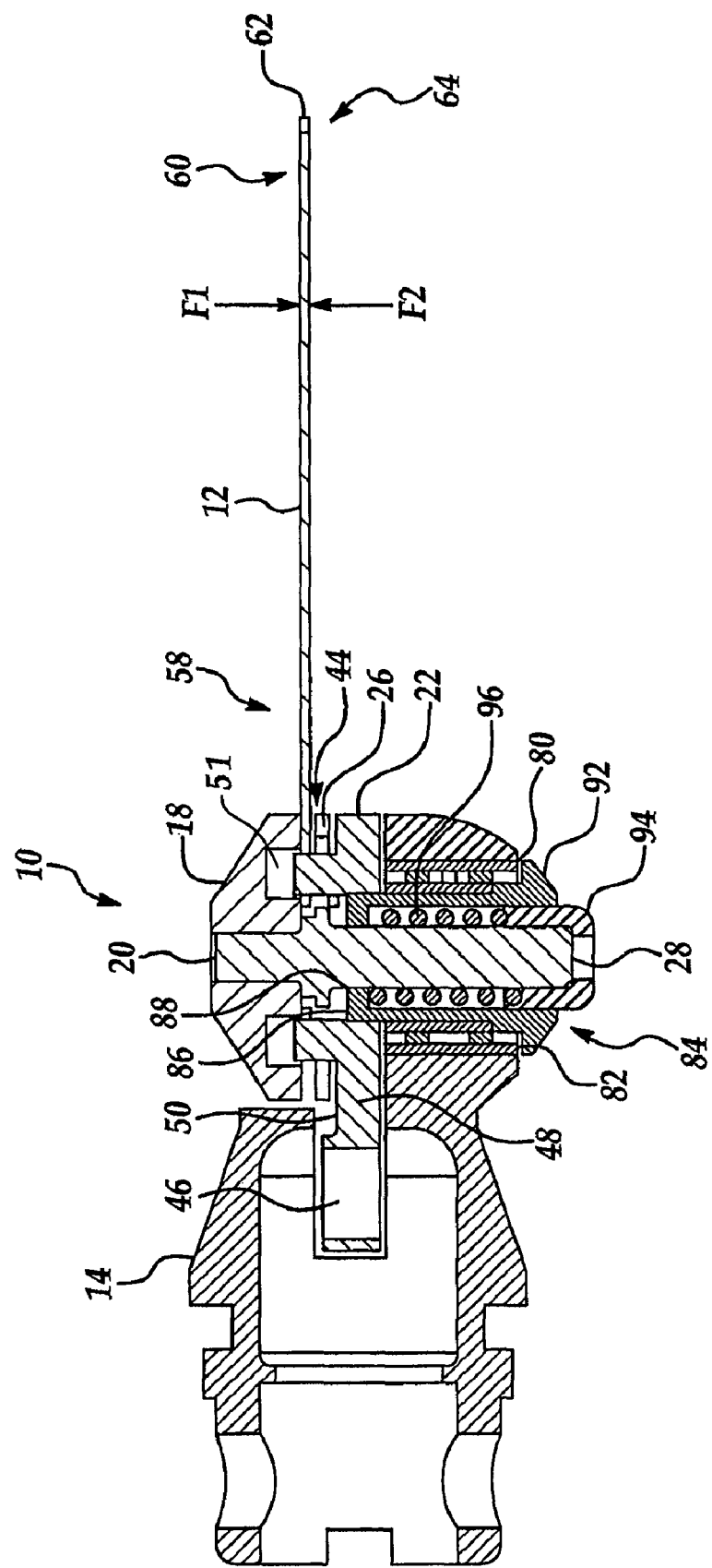
FIG. 3 is a cut-away drawing of the surgical saw blade coupler of FIG. 1 and a straight saw blade.

With specific reference to FIGS. 1, 2, 3 and 7, in one embodiment, the coupler 10 includes a cap 18, a pin 20, and a driver 22. Cap 18 and driver 22 sit on a head 19 which is the most distal end of the housing 14. Pin 20 extends though a bore 82 that extend through the head. The coupler 10 is movable to and between an open position, as shown, in FIGS. 1, 2 and 7, and a closed position, as shown in FIG. 3. When the coupler 10 is in the open position, the surgical saw blade 12 may be removed, positioned or inserted into the coupler 10. The coupler 10 may be moved to the closed position to secure the surgical saw blade 12 in place.

Figure 1:
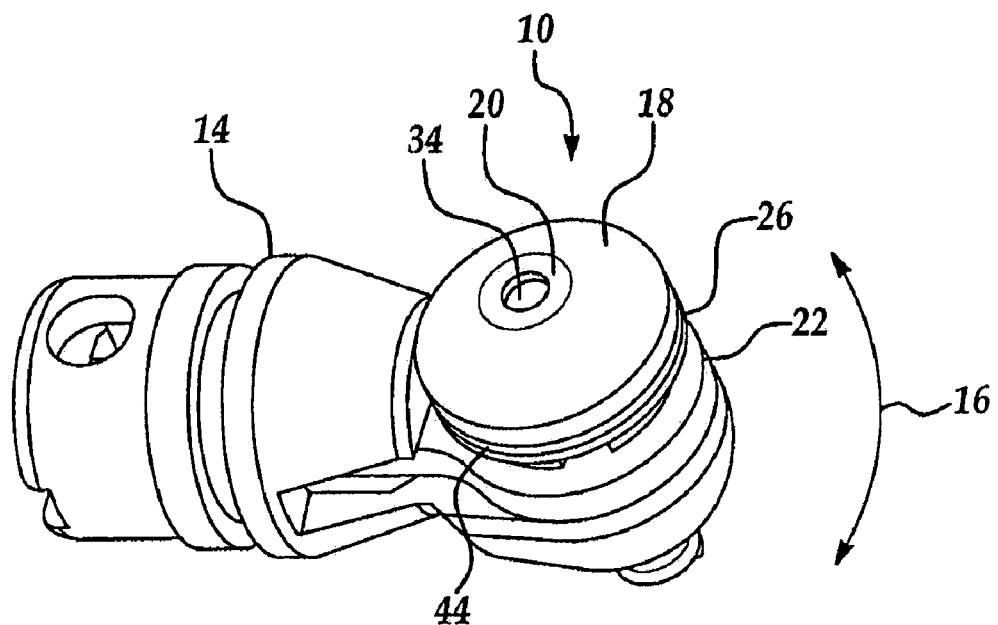
FIG. 1 is an isometric view of a surgical saw blade coupler for use with a surgical saw blade, according to an embodiment of the present invention.
Figure 2:
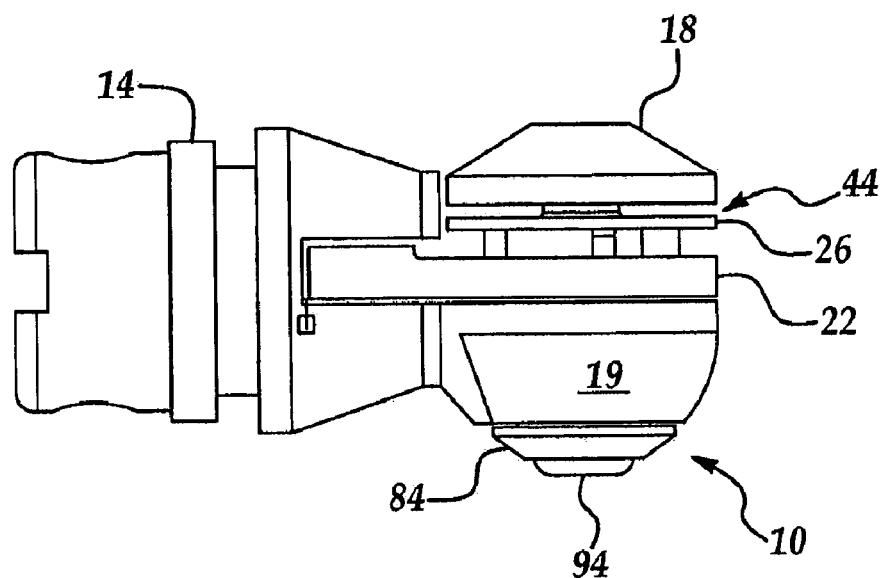
FIG. 2 is side view of the surgical saw blade coupler of FIG. 1.
Figure 5:
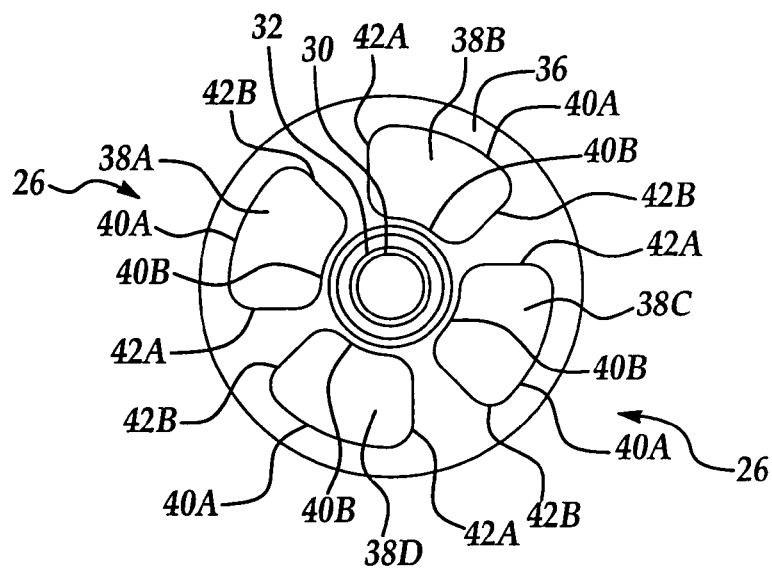
FIG. 5 is a top down view of a pin of the surgical saw blade coupler of FIG. 1, according to an embodiment of the present invention.
Figure 6:
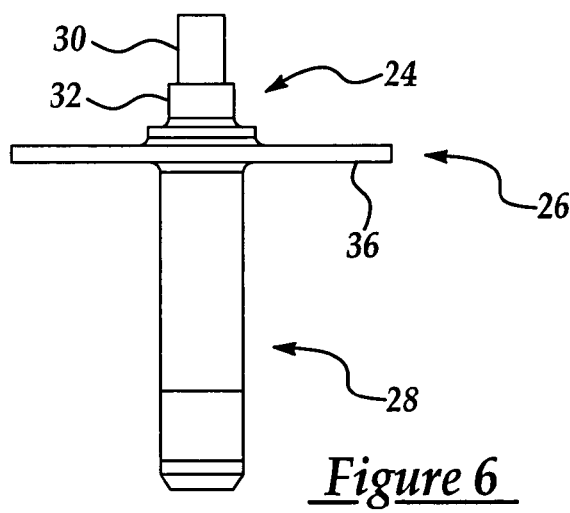
FIG. 6 is a side view of the pin of FIG. 5.
Figure 10:
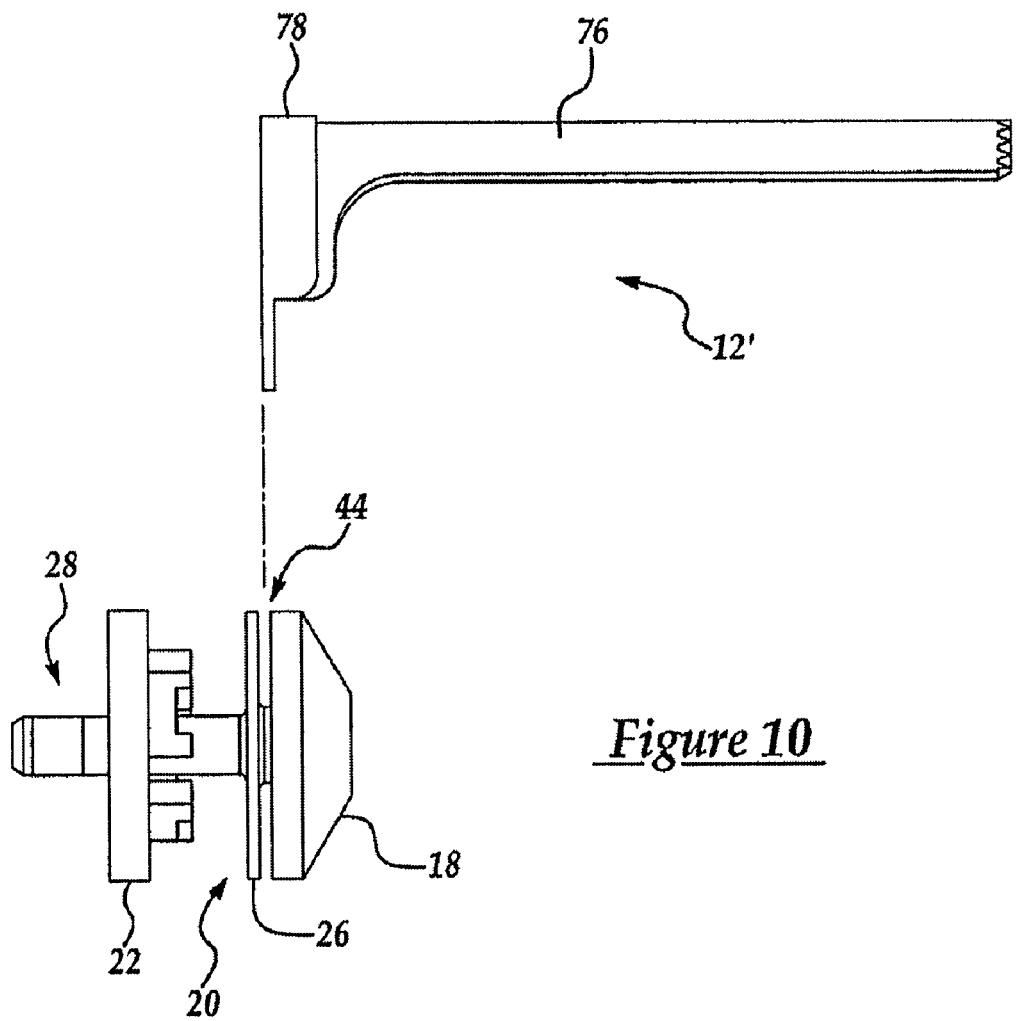
FIG. 10 is a side view of the surgical saw blade coupler and a crescentic saw blade, according to an embodiment of the present invention.

As shown in FIGS. 5 and 6, the pin 20 has an upper portion 24, a circular collar 26, and a bottom portion 28. The upper portion 24 has a cylindrical shape including a top portion 30 and a coupling portion 32. The top portion 30 has a slightly smaller diameter then the coupling portion 32. As shown in FIGS. 1 and 7, the cap 18 includes a cap aperture 34 which receives and secures the coupling portion 32. In one embodiment, the pin 20 and the cap 18 are secured together by a press fit between the cap 18 and the pin upper portion 30.

Returning to FIGS. 5 and 6, collar 26 has a circular outer edge 36. More particularly, the diameter of the collar outer edge 36 is such that the collar extends radially beyond the pin upper and bottom portions 24 and 28, respectively. As shown, the collar 26 includes a plurality of pin apertures 38. In the illustrated embodiment, the circular portion 26 includes four pin apertures 38A, 38B, 38C, 38D. In one embodiment, each aperture 38 has first and second arcuate sides 40A, 40B and first and second linear sides 42A, 42B.

As seen in FIG. 3, cap 18 is shaped to extend over the below-discussed prongs 54A and 54B that are integral with the driver 22. Cap 18 is further shaped to have an opening 51 that extends upwardly from the inner face of the cap, the face directed towards pin collar 26. Opening 51 is aligned with drive 22 to receive prongs 54A and 54B. When joined together, the cap 18 and collar 26 of the pin 20 are spaced apart from each other to form a coupler slot 44 which receives the surgical saw blade 12. Cap 18 may sit on the annular step between pin top portion and coupler portion 32 so that stand off from collar 26 so as to ensure slot 44 is of proper width.

With reference to FIGS. 2, 7, 8 and 9, the driver 22 includes a driven portion 46 and a locking portion 48. In the illustrated embodiment, the driven portion 46 includes first and second prongs and is adapted to couple with the motor and to translate motion from the motor to the coupler 10, and hence, the surgical saw blade 12.

The locking portion 48 includes an upper surface 50 and at least one locking member 52 located on the upper surface 50.

In the illustrated embodiment, driver locking portion 48 has a base (not identified) with an outer surface that is generally planar in shape. The locking portion 48 includes four rigid raised members 56 that are arcuately spaced apart from each other. As shown, each raised member 56 has a general arcuate shape. Raised members 56 are centered around a bore (not identified) that extends through the base of driver locking portion 48. First and second prongs 54A and 54B are integral with each raised member 56. Prongs 54A and 54B extend upwardly from the opposed ends of the raised member 56 with which the prongs are integral. Prongs 54A and 54B are concentric with raised members 56. Driver 22 is further shaped so that prongs 54A and 54B extend above raised members 56.

When the coupler 10 is in the closed position, portions of the first and second engaging prongs 54A, 54B and the central engaging portion 56 of each engaging member 52 fit through one of the pin apertures 38 of the pin 20.

Figure 4:
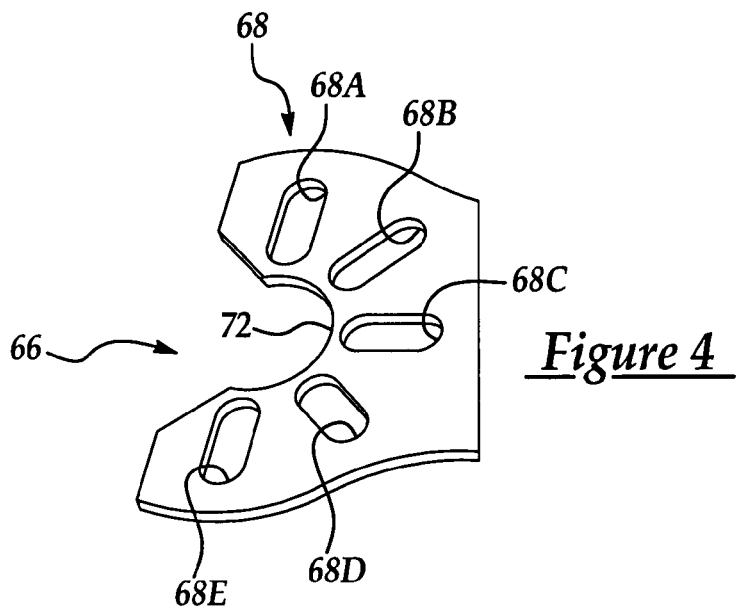
FIG. 4 is a view of a first end portion of a saw blade for use with the surgical saw blade coupler of FIG. 1.

In one illustrated embodiment, the surgical saw blade 12 is a straight blade, as shown in FIGS. 3 and 4. The surgical saw blade 12 has a first end 58 which slides into the coupler slot 44 and is locked into place by the coupler 10 (see below). A second end 60 includes a cutting edge 62 having a plurality of teeth 64.

With particular reference to FIG. 4, the first end 58 includes a blade slot 66 and a plurality of blade apertures 68. In the illustrated embodiment, the first end 58 includes five blade apertures 68A, 68B, 68C, 68D, 68E. The blade apertures 68 are shaped to receive one of the engaging prongs 54 of the locking members 52.

With the coupler 10 in the open position, shown in exaggerated view in FIG. 7, pin 20 is longitudinally positioned relative to housing head 15 and driver locking portion 48 so that collar 26 is disposed above driver prongs 54. When coupling 10 is so positioned, since the coupler slot 44 is clear of the prongs, the surgical saw blade 12 may be inserted into the coupler slot 44 formed between the cap 18 and the pin 20. The blade slot 66 slips around the coupling portion 32 of the pin 20. The surgical saw blade 12 may be positioned within the coupler slot 44 such that the blade apertures 68 align with the engaging prongs 54 of the locking members 52.

Figure 11:
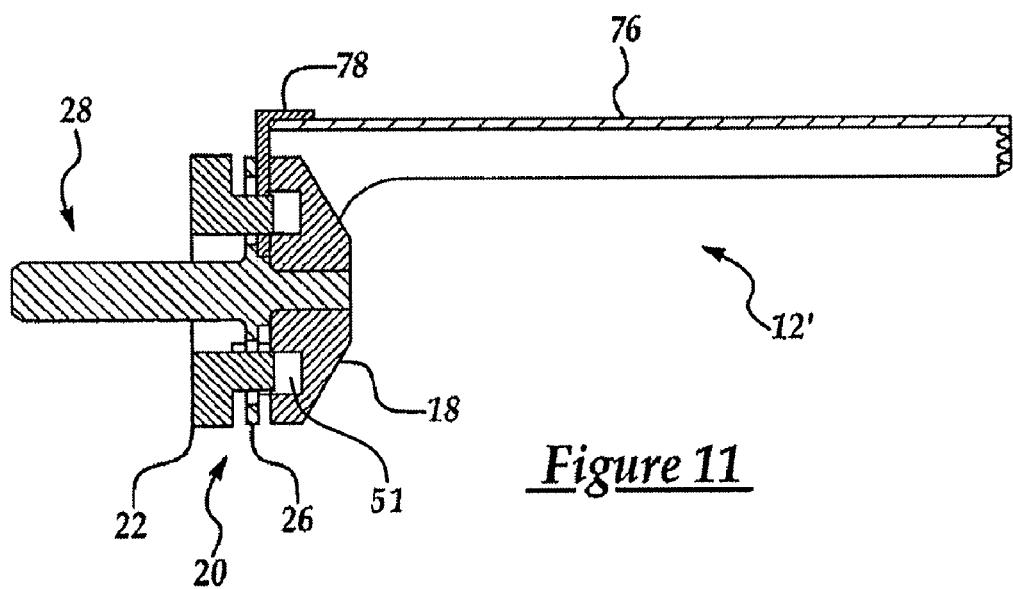
FIG. 11 is a cut away view of the surgical saw blade coupler and the crescentic saw blade of FIG. 10.
Figure 12:
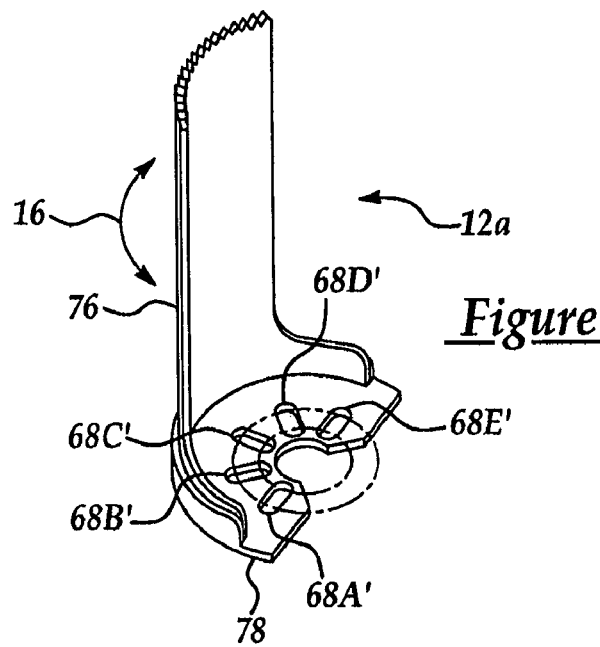
FIG. 12 is an isometric view of the crescentic saw blade of FIG. 11.
Figure 13:
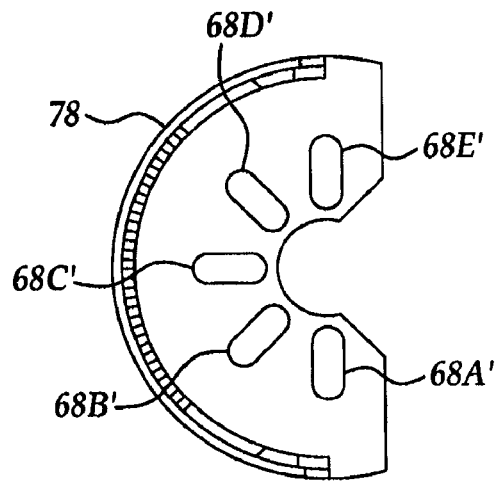
FIG. 13 is a bottom view of the crescentic saw blade of FIG. 11.
Figure 14:
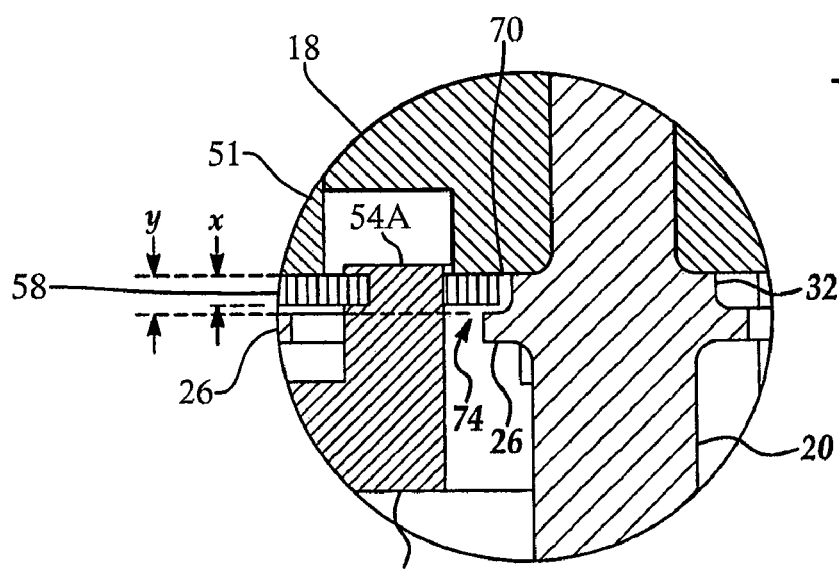
FIG. 14 is an enlarged view of a portion of the surgical saw blade coupler of FIG. 1, according to an embodiment of the present invention.

Once the surgical saw blade 12 is in position, the coupler 10 may be closed or moved to the closed position. FIGS. 3 and 14 are views of the coupler 10 and surgical saw blade 12, when the coupler 10 is in the closed position. When coupler 10 is so positioned, the action of the below-discussed spring 96 against pin 20 holds cap 18 close to driver locking portion 46. Raised members 56, which extend through collar apertures 38, abut the undersurface of the blade 12. Blade 12 is thus compressed between cap 18 and raised members 56. It should be appreciated that the abutment of the blade 12 against the raised members 56 stops the downward movement of the cap 18 towards the drive locking portion 46. Since cap 18 and collar 26 are a single component, the downward movement of the collar is likewise restricted by the abutment of raised members 56 against saw blade 12. Thus, as seen in FIGS. 3 and 11 as a consequence of the downward movement of the collar being blocked, the collar is held above the outer surface of the driver locking portion 46. Prongs 54A and 54B also extend through blade apertures 38. Prongs 54A and 54B are have sufficient length to, as seen in FIG. 3, extend through slot 44 into cap opening 51. More particularly, prongs 54A and 54B extend through blade apertures 68, which are disposed in slot 44 so as to stop lateral movement of the blade 12 out of the slot 44.

The first end 58 of the surgical saw blade 12 has a width, X, which is slightly smaller than the width, Y, of slot 44 between cap 18 and collar 26. For example, in one embodiment, the surgical saw blade 12 has a width of 0.025 inches and slot 44 has a width of 0.027 inches.

When a force is applied to the surgical blade 12 in the direction of arrow F1 or F2, the surgical saw blade 12 tilts within the coupler slot 44. While the surgical saw blade 12 is tilted it is in contact with the coupler slot 44 at two points. One of the corners of the back portion 72 of the surgical saw blade 12 is in contact with either the cap 18 or the pin 20. And a point on the opposite side of the surgical saw blade 12 is in contact with the other of the cap 18 or the pin 20. This helps to prevent further movement of the surgical saw blade 12 within the coupler 10 and to prevent the applied force from opening the coupler 10.

Additionally, the locking members 52 are inserted through the pin apertures 38 in the pin 20. Furthermore, at least one of the engaging prongs 54 is inserted through one of the blade apertures 68 in the first end 58 of the surgical saw blade 12. In the illustrated embodiment, five of the engaging prongs 54 are inserted through the blade apertures 68 in the first end 58 of the surgical saw blade 12. First and second pairs of these engaging prongs 54 are associated with two locking members 52. An upper surface of the central engaging portion 56 engages or is contact with a surface of the first end 58 of the surgical saw blade 12. This serves to lock the surgical saw blade 12 in place between the cap 18 and the pin 20 when the surgical saw blade coupler 10 is in the closed position.

With reference to FIGS. 10, 11, 12, and 13, the surgical saw blade 12 is shown as a crescentic saw blade 12'. The crescentic saw blade 12' has a curved body portion 76 with a first end 58' and a second end 60'. The first end 58' has a cutting edge 62' with a plurality of teeth 64'. A base 78 is connected to the second end 60' of the crescentic saw blade 12'. The base 78 includes a blade slot 66' and a plurality of teeth 64'. The base 78 is similar to the second end 60 of the straight blade 12 detailed above and operates in a similar manner.

In one embodiment, the surgical saw blade 12, 12' are composed from stainless steel.

Returning to FIG. 3, the coupler 10 further includes a bearing 80 inserted into a housing head bore 82 within the housing 14. A cup 84 is inserted within the center of the bearing 80. The cup 84 has a first end 86 and a second end 88. The first end 86 includes a cup aperture 90. A lip 92 is located at the second end 88. The bottom portion 28 of the pin 20 passes through the cup aperture 90. The lip 92 rests against the bearing 80 and prevents further inward (to the left in FIG. 3) movement of the cup 84. A button 94 having a press fit with the bottom portion 28 of the pin 20 is inserted between the bottom portion 28 and the cup 84. A biasing spring 96 is located between the button 94 and the first end 86 of the cup 84. The biasing spring 96 acts against the button 94, and thus, the pin 20, to bias the pin 20 to close the coupler 10. In the illustrated embodiment, the biasing spring 96 acts to close the coupler 10. To insert, remain, and/or exchange blades 12, 12' the cap 18 and pin 20 are manually opened (against the force exerted by the spring 96) by pushing on the button 94. After the blade 12, 12' is removed and/or inserted, the spring 96 acts to close the coupler 10, thus locking the blade 12, 12' in place.

What is claimed is:

1. A surgical saw assembly, said assembly including:
   a housing shaped to receive a motor;
   a head located forward of said housing, said head having a bore;
   a drive plate disposed over said head, said drive plate having: at least one feature that connects said drive plate to the motor so that said drive plate oscillates around an axis concentric with the head bore; an outer surface spaced from said head; a plurality of spaced apart prongs that extend upwardly from the drive plate outer surface a first distance, said prongs spaced apart from each other so as to seat in openings formed in a saw blade; and at least one rigid raised member that extends upwardly from the drive plate outer surface a second distance, the second distance being less than the first distance, said raised member positioned so that when said prongs are disposed in the blade openings, said raised member is seated under the saw blade;
   a pin disposed in the head bore so as to move longitudinally in the bore, said pin having an upper end located above said drive plate;
   a collar mounted to the upper end of said pin so as to move with said pin, said collar being located above said drive plate and having openings through which said drive plate prongs and said at least one raised member can extend through;
   a cap mounted to the upper end of said pin to move with said pin so as to be spaced above said collar so as to define a slot between said collar and said cap for receiving a saw blade, said cap shaped to extend radially outwardly beyond the drive plate prongs and having an inner surface that faces said collar and an opening that extend inwardly from the inner surface for receiving the drive plate prongs; and
   a biasing member that extends between said head and said pin that displaces said pin so that said cap is urged towards said drive plate,
   wherein said drive plate prongs and said at least one raised member are further dimensioned and said pin, said cap and said collar are further arranged so that:
   when a saw blade is disposed in the slot and said cap is positioned proximal to said drive plate, said at least one raised members abuts the saw blade so that the saw blade is compressed between said raised member and said cap and said drive plate prongs extend through and above said collar, through the saw blade openings and into the opening in said cap; and
   said pin can be moved relative to said head so that said collar can be positioned at least partially above said drive plate prongs.

2. The surgical saw assembly of claim 1, wherein a plurality of said raised members extend above the outer surface of drive plate.

3. The surgical saw assembly of claim 1, wherein a plurality of said raised members extend above the outer surface of said drive plate and each said raised member is integral with at least one said prong.

4. The surgical saw assembly of claim 1, wherein:
   a plurality of said raised members extend above the outer surface of drive plate; and
   said prongs and said raised members are arranged and said collar is shaped so that each collar opening receives at least one said prong and at least one said raised member.

5. The surgical saw assembly of claim 1, wherein said drive plate prongs are arcuately spaced apart from each other around a common circle.

6. The surgical saw assembly of claim 1, wherein:
   said drive plate is formed with a bore concentric with the head bore;
   said pin extends through the drive plate bore; and
   said drive plate prongs are arcuately spaced apart from each other around a circle that is concentric with the drive plate bore.

7. The surgical saw assembly of claim 1, wherein said biasing member is a spring that extends between said head and said pin.

8. A surgical saw assembly, said assembly including:
   a housing shaped to receive a motor;
   a head located forward of said housing;
   a drive plate, said drive plate having: a locking portion with an outer surface disposed above said head; and a drive portion configured to be driven by the motor so that when the motor is actuated the drive portion oscillates the locking portion around an axis that extends through the locking portion;
   a collar located above the drive plate locking portion outer surface that is longitudinally moveable relative to the drive plate locking portion, said collar shaped to have a plurality of openings;
   a cap integral with said collar that is located above said collar so as to define a slot between said collar and cap that is dimensioned to receive a saw blade, said cap having an inner face that is directed towards said collar and an opening that extends inwardly from the inner face;
   a retaining assembly that extends between said cap and said head for releasably holding said cap in a position proximal to the drive plate locking portion;
   a plurality of prongs integral with the drive plate locking section, said prongs having positioned to extend through the collar openings into the cap opening and having a height so that,
   when said cap is located proximal to the drive plate locking portion, said prongs extend through the collar openings and the slot into the cap opening; and
   when said cap is displaced relative to the drive plate locking portion so as to spaced from the drive plate locking portion, said collar rises above said prongs;
   at least one rigid raised member integral with the drive plate locking section that has height less than the height of said prongs and positioned to extend through one of the collar openings; and a saw blade having a first end with teeth and a second end spaced from the first end, the second end dimensioned to seat in the slot between said collar and cap, the saw blade second end shaped to have a plurality of openings arranged so that, when the second end is in the slot and said cap is located proximal to the drive plate locking portion: said prongs extend through the saw blade openings; and the at least one drive raised member abuts the saw blade so that the saw blade is compressed between said at least one raised member and said cap.

9. The surgical saw assembly of claim 8, wherein said at least one raised member is positioned on said drive plate locking portion and said collar is shaped so that said at least one raised member extends through a collar opening through which at least one said prong extends.

10. The surgical saw assembly of claim 8, wherein a plurality of said of said raised members extend above the outer surface of the drive plate locking portion and said raised members extend through the collar openings through which said prongs extend.

11. The surgical saw assembly of claim 8, wherein:
a pin integral with said collar and said cap extends away from said collar across the drive plate locking section into said head and is moveably mounted to said head; and
said retaining assembly extends between said head and said pin so as to releasably hold said pin in said head in position in which said cap is located proximal to the drive plate locking portion.

12. The surgical saw assembly of claim 8, wherein:
a pin integral with said collar and said cap extends away from said collar across the drive plate locking section into said head; and
said retaining assembly includes a spring that extends between said pin that biases said pin so that said pin holds said cap proximal to the drive plate locking portion.

13. The surgical saw assembly of claim 8, wherein said retaining assembly includes a spring that extends between said head and said cap that holds said cap proximal to the drive plate locking portion.

14. The surgical saw assembly of claim 8, wherein a plurality of said of said raised members extend above the outer surface of the drive plate locking portion, said prongs and said raised members being arranged so that two prongs are integral with each said raised member, said prongs being located at opposed ends of the said raised member with which said prongs are integral.

15. A surgical saw assembly, said assembly including:
a housing shaped to receive a motor;
a head located forward of said housing;
a drive plate, said drive plate having: a locking portion with an outer surface disposed above said head; a drive portion configured to be driven by the motor so that, when the motor is actuated, the drive portion oscillates the locking portion around an axis that extends through the locking portion; and a plurality of rigid raised members that extend upwardly from the outer surface of the locking portion;
a collar located above the drive plate locking portion that is longitudinally moveable relative to the drive plate locking portion, said collar shaped to have a plurality of openings, the openings being positioned so that said raised members can extend therethrough;
a cap integral with said collar that is located above said collar so as to define a slot between said collar and cap, the slot dimensioned to receive a saw blade, said cap having an inner face that is directed towards said collar and an opening that extends inwardly from the inner face;
a retaining assembly that extends between said collar and said head for releasably holding said cap in a position in which said cap is proximal to the drive plate locking portion so that when said cap is so positioned, a saw blade disposed in the slots is compressed between said raised members and said cap; and
a plurality of prongs integral with the drive plate locking section that extend upwardly from the outer surface of the drive plate locking section so as to extend above said raised members, said prongs positioned to extend through the collar openings into the cap opening and having a height so that,
when said cap is positioned proximal to the drive plate locking portion, said prongs extend through said collar openings, openings in the saw blade seated in the slot and into the cap opening; and
when said cap is displaced from the position proximal to the drive plate locking portion to a position distal to the drive plate locking portion, said collar rises at least partially above said prongs so that the saw blade can be removed from the slot.

16. The surgical saw assembly of claim 15, wherein each said raised member is integral with at least one said prong.

17. The surgical saw assembly of claim 15 wherein said prongs are arcuately spaced apart from each other around a common circle.

18. The surgical saw assembly of claim 15, wherein:
the drive plate locking section is formed with a through bore;
said prongs are arcuately spaced apart from each other around a common circle centered on the through plate bore;
a pin integral with said cap and said collar extends from said collar through said drive plate through bore into the head; and
said retaining assembly extends between said head and said pin so as to releasably hold said pin in said head in position in which said cap is positioned proximal to the drive plate locking portion.

19. The surgical saw assembly of claim 15, wherein said retaining assembly includes a spring that holds said cap in the position proximal to the drive plate locking portion.

20. The surgical saw assembly of claim 15, wherein:
the drive plate locking section is formed with a through bore;
said raised members and said pins are arranged in a common circle centered on the through plate bore and are further arranged so that one said prong extends upwardly from each arcuately opposed end of each said raised member;
said collar is shaped so that each said member and the two said prongs associated with said raised member extend through a separate opening forming in said collar;
a pin integral with said cap and said collar extends from said collar through said drive plate through bore into the head; and
said retaining assembly extends between said head and said pin so as to releasably hold said pin in said head in position in which said cap is positioned proximal to the drive plate locking portion.

* * * * *